(12) United States Patent
van Wuijckhuijse et al.

(10) Patent No.: US 8,723,106 B2
(45) Date of Patent: May 13, 2014

(54) METHOD AND APPARATUS FOR IDENTIFICATION OF BIOLOGICAL MATERIAL

(75) Inventors: Arjan Laurens van Wuijckhuijse, Zwijndrecht (NL); Rene Parchen, Delft (NL)

(73) Assignee: Nederlandse Organsatie Voor Toegepast Natuurwetenschappelijk Onderzoek Tno, Delft (NL)

( * ) Notice: Subject to any disclaimer, the term of this patent is extended or adjusted under 35 U.S.C. 154(b) by 361 days.

(21) Appl. No.: 13/059,947

(22) PCT Filed: Aug. 21, 2009

(86) PCT No.: PCT/NL2009/050508
§ 371 (c)(1),
(2), (4) Date: May 6, 2011

(87) PCT Pub. No.: WO2010/021548
PCT Pub. Date: Feb. 25, 2010

(65) Prior Publication Data
US 2011/0204220 A1    Aug. 25, 2011

(30) Foreign Application Priority Data
Aug. 21, 2008 (EP) ..................................... 08162783

(51) Int. Cl.
*B01D 59/44* (2006.01)
(52) U.S. Cl.
USPC .......................................... 250/282; 250/281
(58) Field of Classification Search
None
See application file for complete search history.

(56) References Cited

U.S. PATENT DOCUMENTS

| | | | | |
|---|---|---|---|---|
| 4,499,052 A | * | 2/1985 | Fulwyler | 422/52 |
| 4,538,733 A | * | 9/1985 | Hoffman | 209/3.1 |
| 4,691,829 A | * | 9/1987 | Auer | 209/3.1 |
| 4,778,593 A | * | 10/1988 | Yamashita et al. | 209/3.1 |
| 4,981,580 A | * | 1/1991 | Auer | 209/3.1 |

(Continued)

FOREIGN PATENT DOCUMENTS

| WO | WO 02/052246 A2 | 7/2002 |
|---|---|---|
| WO | WO 2008/080224 A1 | 7/2008 |

OTHER PUBLICATIONS

Wuijckhuijse, A.L. Van, et al., "Matrix-assisted laser desorption/ionisation aeresol time-of-flight mass spectrometry for the analysis of bioaerosols: development of a fast detector for airborne biological pathogens," Journal of Aerosol Science, Pergamon, vol. 36, No. 5-6, pp. 677-687, (May 1, 2005).

(Continued)

Primary Examiner — Andrew Smyth
(74) Attorney, Agent, or Firm — Kilpatrick Townsend & Stockton LLP (57) ABSTRACT

Biological material is detected in a sample using a MALDI-MS technique (Matrix Assisted Laser Desorption and Ionization-Mass Spectroscopy). A liquid comprising the sample and a MALDI matrix material is prepared and used to form a continuous stream of the liquid. The stream is separated into successive parts to form drops, which are launched into flight, or the stream is launched into flight and then separated into drops. Drop forming techniques may be used that are known from ink jet printers. Material from the drops is ionized while in flight. Mass spectra from the ionized material of respective drops are measured. Preferably, before the drops are formed the liquid is diluted to a level where the majority of drops at most one micro-organism is present per drop.

15 Claims, 5 Drawing Sheets

(56) References Cited

U.S. PATENT DOCUMENTS

| | | | |
|---|---|---|---|
| 5,747,349 A * | 5/1998 | van den Engh et al. | 436/172 |
| 5,873,523 A * | 2/1999 | Gomez et al. | 239/3 |
| 6,281,018 B1 * | 8/2001 | Kirouac et al. | 436/63 |
| 6,555,360 B1 | 4/2003 | Srienc et al. | |
| 6,793,642 B2 * | 9/2004 | Connelly et al. | 604/5.01 |
| 6,880,414 B2 * | 4/2005 | Norton | 73/865.5 |
| 6,918,309 B2 * | 7/2005 | Brock et al. | 73/863.32 |
| 7,186,502 B2 * | 3/2007 | Vesey | 435/4 |
| 7,201,875 B2 * | 4/2007 | Norton et al. | 422/73 |
| 7,544,326 B2 * | 6/2009 | Norton et al. | 422/73 |
| 7,671,330 B2 * | 3/2010 | Reilly et al. | 250/290 |
| RE41,780 E * | 9/2010 | Anderson et al. | 435/91.2 |
| 8,003,934 B2 * | 8/2011 | Hieke | 250/288 |
| 2004/0156755 A1 * | 8/2004 | Wardlaw | 422/102 |
| 2005/0218319 A1 * | 10/2005 | Bandura et al. | 250/288 |
| 2005/0230615 A1 * | 10/2005 | Furutani et al. | 250/287 |
| 2008/0147443 A1 | 6/2008 | Scherpbier et al. | |
| 2008/0187466 A1 * | 8/2008 | Wardlaw | 422/102 |

OTHER PUBLICATIONS

Stowers, M.A., et al., "Fluorescence preselection of bioaerosol for single-particle mass spectrometry," Applied Optics, OSA, Optical Society of America, vol. 45, No. 33, pp. 8531-8536 (Nov. 20, 2006).

Fei, Xun, et al., "Aerosol MALDI with a Reflectron Time-of-Flight Mass Spectrometer," Analytical Chemistry, American Chemical Society, vol. 68, No. 7, pp. 1143-1147 (Apr. 1, 1996).

Hinz, Klaus-Peter, et al., "Instrumentation, data evaluation, and quantification in on-line aerosol mass spectrometry," Journal of Mass Spectrometry, John Wiley and Sons, Ltd., vol. 42, No. 7, pp. 843-860, (Jul. 2007).

Russell, Scott C., "Microorganism Characterization by Single Particle Mass Spectrometry," Mass Spectrometry Reviews, John Wiley and Sons, Inc., USA, vol. 28, No. 2, pp. 376-387 (Mar. 2009).

\* cited by examiner

METHOD AND APPARATUS FOR IDENTIFICATION OF BIOLOGICAL MATERIAL

CROSS-REFERENCES TO RELATED APPLICATIONS

This application is a National Stage of International Application No. PCT/NL2009/050508, filed Aug. 21, 2009, and which claims the benefit of European Patent Application No. 08162783.8, filed Aug. 21, 2008, the disclosures of which are incorporated herein by reference.

FIELD OF THE INVENTION

The invention relates to identification of biological material in liquids.

BACKGROUND

It is known to use mass-spectroscopy for the identification of biological material such as micro-organisms (e.g. bacteria, virusses), cells, peptides etc.

MALDI-MS (Matrix Assisted Laser Desorption-Ionization-Mass Spectroscopy), for example, involves laser ionization of sample material containing micro-organisms and mass spectroscopic analysis of the ionized particles. In MALDI-MS the micro-organisms are prepared for ionization by providing a mixture of micro-organisms and matrix material on a target plate. While the mixture dries, the matrix material attaches to the micro-organisms, which enables soft ionization with relatively low energy that preserves large molecular fragments for the analysis constituents of the micro-organisms. Laser shots are fired at selected target locations on the target plate in order to ionize material from these target locations. For each target location a mass spectroscopic analysis of the resulting is performed.

MALDI-MS has been found to be very suitable for laboratory analysis, but several problems remain. For samples with an inhomogeneous mix of micro-organisms there is a serious risk that a single laser shot ionizes material from a mix of micro-organisms of different species, which complicates the identification of individual species. Even if an isolated single micro-organisms could be found on the target plate, it would not be possible to detect it in the noise of all material ionized by a laser shot. In MALDI-MS these problems are overcome by using an initial breeding step when the original sample, taken for example from patient in vivo, contains an inhomogeneous mix of micro-organisms. Breeding may be used to ensure that a substantial number of micro-organisms of mainly one strain are produced within a single laser shot. However, breeding may take over a day. As a result, practical MALDI-MS is not suitable if a short turn around time is needed between taking an in vivo sample and providing an analysis result. This limits its applicability.

For example, in an example before transferring an incoming patient to an environment where the MRSA bacteria could do harm, it would be desirable to obtain a sample from the patient, and identify MRSA bacteria among the many micro-organisms present in the sample. To be of practical use, a result of such a measurement should preferably be available within a few hours at most. The need to breed micro-organisms prevents practical use of conventional MALDI-MS for this purpose.

The use MALDI-MS for identification of micro-organisms is known from an article titled "Matrix-assisted laser deporption/ionization aerosol time of flicght mass spectroscopy for the analysis of bioaerosols: development of a fast detector for airborne biological pathogens" by A. L. van Wuijckhuijse et al and published in the Journal of Aerosol Science Vol 36 pages 677-697 (EPO reference XP004936536). This document describes the use of a nebulizer to nebulize solutions that were produced by diluting mono-culture bacterial samples to predetermined values. The nebulization mentioned in this document does not guarantee drops of a uniform size. As a result the number of bacteria per drop may vary, but this did not matter as only one species of bacteria was used. Moreover, the nebulization method of this document requires that a large sample volume is available, even if distributed over small drops.

From WO02052246 an apparatus for detecting and identifying bioaerosol particles in the air is known. This apparatus collects air containing bioaerosol particles, and feeds the air with the particles through a nozzle into an analysis chamber. In the analysis chamber particles with microorganisms are detected and the detected particles are ionized. The apparatus requires a relatively large number of particles, because many particles are lost in the transition from air pressure to the high vacuum used from mass spectroscopy. The efficiency of examined particles to captured particles may be as low as one percent.

From U.S. patent application 2005/0230615 a MALDI-IM (Ion Mobility) measurement technique is known wherein drops are formed with a Vibrating Orifice Aerosol Generator. Nothing is disclosed about micro-organisms in the drops. If the drops would contain micro-organisms, use of MALDI-IM would make it difficult if not impossible to identify these micro-organisms.

The use of Flow Field-Flow Fractionation (FFFF) in the preparation of a target plate for MALDI-MS is known from an article by Hookeun Lee et al, titled "Analysis of Whole Bacterial Cells by Flow-Field Flow Fractionation and Matrix-Assisted Laser Desorption/Ionization Time-of-Flight Mass Spectroscopy" and published in Anal. Chem. 2003, 75, 2746-2752. This document shows that FFFF can be used to separate intact bacterial cells to increase cell density for MALDI-MS, when a target plate is used.

SUMMARY

Among others it is an object of the invention to provide for a method and apparatus for identifying biological material that can provide results quickly based on a liquid sample with a mix of different types of micro-organisms, such as bacteria, fungi and viruses.

A method of identifying biological material that comprises micro-organisms in a sample is provided, the method comprising
- preparing a liquid comprising the sample and a MALDI matrix material;
- generating a continuous stream of the liquid;
- separating the stream into successive parts of the stream, to form flying drops;
- diluting the liquid to a dilution level dependent on a measured density of the micro-organisms, to a dilution level corresponding to a density C of microorganisms that satisfies $C*V<1$, wherein V is a volume per separated part;
- ionizing material from the drops while in flight;
- measuring mass spectra from the ionized material.

Herein flying drops of liquid are formed, by separating a stream of liquid comprising biological material from a sample and MALDI matrix material, for example a crystal forming matrix material, into successive parts of the stream.

An active drop former may be used for example, with a piezo-electric element. Ionization and mass spectroscopy is performed on the drops while in flight. In this way the need for a target plate and its disadvantages can be eliminated, while a high efficiency is realized. The drops may dry in flight so that the dried drops are dried particles when they are ionized. As used herein, the term "drop" includes the dried particles formed by drying the drops. Preferably, mass spectra are measured each for the material from a respective one of the drops.

The sample or the liquid is diluted to a dilution level corresponding to a concentration in which the density C of micro-organisms satisfies $C*V<1$, where V is a volume of said parts of the liquid. Thus less than one micro-organism or cell will occur on average in a drop volume in an individual drop. Thus, it may be ensured that a considerable number of measurements of drops with a single micro-organism or cell per drop can be obtained. As a result, mass spectra for individual micro-organisms and/or cells can be obtained.

In an embodiment the dilution level may be adapted to the concentration of cells and/or micro-organisms in the sample. A density detector may be used to measure the concentration, for example by counting detected micro-organisms, and the measured concentration may be used to control dilution. The density detector may comprise a (flow) cytometer located to detect the density in the stream, for example by counting micro-organisms in the stream, or in a precursor stream that flows into the stream when the MALDI matrix is added to the precursor stream.

In an embodiment, the stream flows to the drop former without any substantial axial rearrangement after the point where the stream with sample and matrix material is generated. That is, that parts into which the liquid is separated correspond to successive sections of the stream already once the matrix material has been added, or at least after dilution. In this way the probability of drops with multiple micro-organisms is reduced. This is improved by measuring the density in this stream with a cytometer and controlling the dilution based on this measurement. In an embodiment the dilution may be performed by mixing carrier liquid into the stream downstream from the generation of the stream. This also reduces the probability of drops with multiple micro-organisms.

In an embodiment an apparatus for identifying biological material in a sample, the apparatus comprising
- a stream generator configured to supply a continuous stream of a liquid wherein the sample and a MALDI matrix material have been mixed;
- a mixing unit comprising a mixer and a detector for measuring a density of micro-organisms, a dilution level of the mixer being controlled dependent on a measured density of the micro-organisms, to a dilution level corresponding to a concentration C of microorganisms that satisfies $C*V<1$, wherein V is a volume per separated part;
- a liquid portion separator configured to separate the stream into successive parts of the stream and to supply drops formed from said parts in flight along a flight path;
- a radiation source directed at the flight path and configured to supply radiation for ionizing material from the drops;
- a mass spectrometer configured to obtain mass spectrograms of the ionized material from individual ones of the drops. The liquid portion separator may be a drop former, comprising a piezo-electric resonator for example.

In another embodiment the liquid portion separator of the apparatus comprises a gas stream supply outlet and a conduit for supplying a stream of the liquid into the outlet configured to form a gas dynamic nozzle.

In another embodiment the apparatus comprises a diluting unit configured to add diluent to the sample or the liquid to a dilution level corresponding to a concentration of less than one micro-organism on average in a drop volume of individual ones of the drops. Alternatively, a concentration may be used at which a majority of drops contains at most one micro-organism from the sample. In a further embodiment the dilution unit comprises a density detector configured to detect a density of the sample or the liquid with the sample and to control dilution to said level dependent on the detected density.

In an embodiment, the liquid portion separator may be configured to launch the drops directly into the vacuum space in which the ionization is performed.

In another embodiment the apparatus comprises a control unit configured to synchronize drop formation and pulse generation from the radiation source.

BRIEF DESCRIPTION OF THE DRAWING

These and other objects and advantageous aspects will become apparent from a description of exemplary embodiments.

DETAILED DESCRIPTION OF EXEMPLARY EMBODIMENTS

Figure 1:
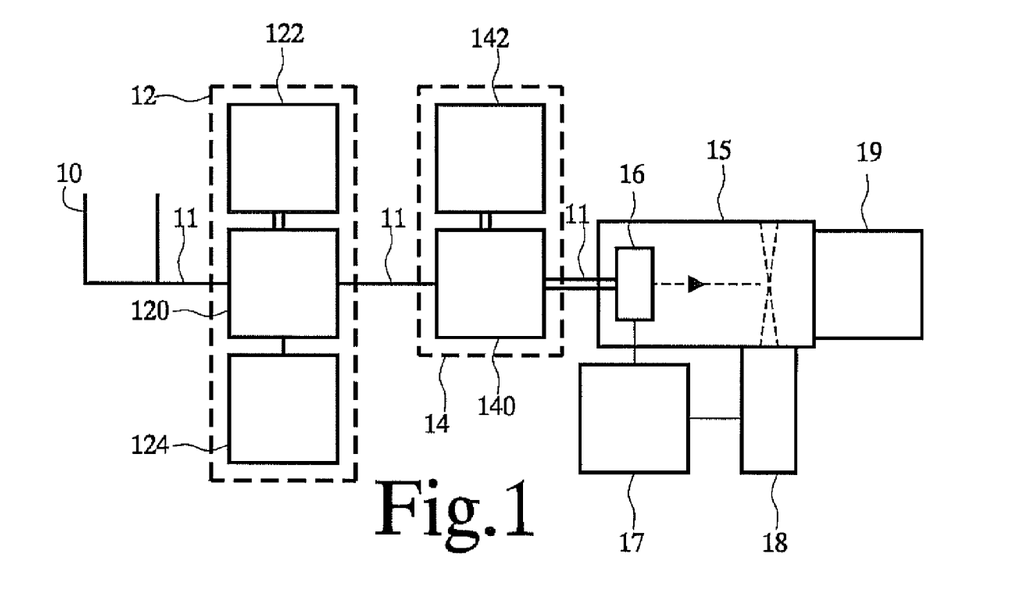
FIG. 1 shows an apparatus for identifying micro-organisms

FIG. 1 schematically shows an apparatus for identifying biological material. Although an application to identification of micro-organisms will be described in the context of this apparatus, it should be appreciated that the apparatus is only one embodiment of an apparatus that performs MALDI mass spectroscopy on flying droplets. It should be understood that other biological material may be used instead of micro-organisms, such as cells (e.g. blood cells, peptides etc.).

The apparatus comprises a sample receiver 10, conduits 11, a first mixing unit 12, a second mixing unit 14, a chamber 15, a piezo resonator 16, a control circuit 17, a pulse laser 18 and a mass spectrometer 19. Piezo resonator 16 may be of a type used in inkjet printers to form drops of ink. Conduits 11 connect sample receiver 10, first mixing unit 12, second mixing unit 14 and piezo resonator 16 in series. Control circuit 17 is coupled to piezo resonator 16 and pulse laser 18.

Piezo resonator 16 is located in chamber 15. Conduit 11 from second mixing unit 14 discharges into an opening through piezo resonator 16. Pulse laser 18 is directed at a flight path of droplets launched from this opening through chamber 15. Mass spectrometer 19 is attached to chamber 15 and located to receive ionized fragments that result from absorption of radiation from pulse laser 18 by droplets in the flight path.

In operation a stream of liquid, containing sample material from sample receiver 10, diluent from first mixing unit 12 and matrix material from second mixing unit 14, is separated into sections that each result in a small liquid drop launched in flight through chamber 15. During flight through chamber 15 the matrix material in a liquid drop crystallizes around a micro-organism while the drop dries in flight, resulting in a dried particle. Subsequently, a laser pulse is fired at the dried particle from pulse laser 18. This results in ionization of material from the dried particle. The ionized material is analyzed in mass spectrometer 19.

Drops with a diameter in a range of 1-100 micrometer may be used for example. Preferably, drops having substantially a same uniform size in this range are used, which may be realized by breaking up the stream of liquid at regular distances, for example by applying a periodic disturbance of appropriate frequency on a stream of constant average flow rate.

Because of the small size of the drops, only little time during flight is needed the drops are prepared for ionization. Because the preparation occurs in flight, micro-organisms with matrix material surrounding a micro-organism on all sides may be formed. No crystallization nuclei occur at the interface between drops and a target plate, as in the case of conventional MALDI-MS. Preferably, the combination of the dilution rate and drop size is selected so that most drops with a microorganism contain no more than one microorganism. For example, a dilution level corresponding to a concentration of at most one micro-organism on average in the volume of a drop may be used.

Because pulsed laser 18 is fired at one dried particle at a time, each measured mass spectrum of a particle from a drop with one micro-organism represents one micro-organism only. Moreover, the use of drops means that the size of the sample that is ionized is determined by the drop size and the amount of dissolved and dispersed material inside the drop. This should be contrasted with conventional MALDI-MS, wherein the size of the sample is determined by the size of the laser spot on the target plate, which may be much larger than the size of drops, so that more material is ionized that can lead to an increased "noise"-level in the mass spectrum. Also, a mix of different micro-organisms may be ionized.

An experiment was conducted to show that individual Staphylococcus Aureus with and without penicillin resistance could be distinguished. In this experiment aerosolization of liquid containing sample material, diluent and matrix material was used. Individual particles (vacuum dried droplets) were ionized with a pulsed laser and a mass spectrum of the ionized material was obtained. It was found that particles with Staphylococcus Aureus with penicillin resistance and particles with Staphylococcus Aureus without penicillin resistance could be distinguished based upon their mass spectra.

First mixing unit 12 serves as a dilution unit. It comprises a first mixer 120, a diluent reservoir 122 and a detector 124. Diluent reservoir 122 is coupled to first mixer 120 to supply diluent and first mixer 120 is configured to mix the diluent with sample material from sample receiver 10. Detector 124 may be an optical detector configured to detect light scattered from individual micro-organisms when the micro-organisms flow through a measurement beam, for example in a conduit through which liquid with the micro-organisms is circulated. From a count of micro-organisms that are detected on average per unit time interval, the density may be determined. In another embodiment an optical scattering intensity may be measured from liquid in first mixer 120 containing diluent and material from sample receiver 10.

Detectors of this type are known per se. A known type of cytometer, or flow cytometer may be used. As is known per se, a cytometer may be a device that detects local fluctuations of biological material density corresponding to difference between the spatial concentration of material in individual micro-organisms against the background of neighboring liquid. For example, temporal fluctuations may be detected at a location through which a flow of liquid with the micro-organisms occurs, or spatial fluctuations may be detected by scanning a detection location. On optical detection may be used for example, using a device that provides for the detection of fluorescence or other optical properties focused in a small region with a size less than a maximum liquid volume per micro-organism. One or more detectors may be used that detect fluorescence at wavelengths at which material such as NADH fluoresces that is characteristic of micro-organisms. Other optical properties, such as scattering, diffraction etc. may also be used.

Particle detector 124 is shown coupled to a control input of first mixer 120. The control mechanism is arranged to increase the amount of diluent added to the sample until the measured density has dropped to or below a predetermined density. A liquid circulation circuit may be used to circulate the diluted sample along a diluent injection point until the desired density has been achieved. In practice, a control computer (not shown) may be used to receive measurement data from density detector 124 and to generate mixer control signals based on this data.

In operation a liquid sample containing micro-organisms is provided in sample receiver 10. A pump (not shown) pumps sample material to first mixing unit 12 through conduit 11. First mixer 120 adds diluent to the sample material. Water or ethanol may be used as diluent for example. Batch-wise processing may be used, wherein a batch of sample material is supplied to first mixing circuit 12, after which processing continues with that batch, without obtaining further material from sample receiver 10 until the batch has been processed and has left first mixing unit 12. A batch size in a range from 0.01 to 10 milli-liters may be used for example.

A feedback loop is used to increase the dilution rate until the density observed by density detector 124 has dropped to a predetermined level. Instead of feedback, a feed forward solution may be used, wherein the initial density is measured and the resulting level is used to control the amount of added diluent to the predetermined level. In an embodiment the predetermined level is selected so that a majority of the drops will contain one micro-organism or less. The level may be set so that on average of less than one micro-organism per drop is achieved, or an average between four and one quarter micro-organism per drop. It should be noted that an overall count of micro-organisms in the liquid suffices, unspecific for the type of microorganism. Thus a reasonable number of drops with only one micro-organism of any type can be ensured.

The actual level may be selected in combination with the size of the drops, which is controlled by the setting of parameters of droplet formation, using a relation between measurements from detector 124 and the concentration of micro-organisms. In one embodiment, this level may be set experimentally during a calibration step, based on observations of the fraction of drops in which material from micro-organisms is observed by mass-spectroscopy, by adjusting the level until the fraction of drops containing one micro-organism is at a predetermined level of for example one tenth to half of the generated mass spectra. In one example a dilution up to a dilution ratio between one to five sample to diluent may be used.

It should be noted that the feedback in first mixing unit 14 serves to ensure that samples with different concentrations of micro-organisms do not result in large changes in efficiency, in terms of the number of useless droplets that contain no micro-organisms, or in a considerable number of droplets that contain more than one organism. If the concentration can be controlled beforehand, no feedback or density determination may be needed. Similarly, feedback or density determination 
may be omitted if it is known that the concentration is not so high that a risk of a considerable number of droplets with multiple organisms persists after a predetermined dilution, and a loss of efficiency is accepted. In this case a predetermined dilution rate may be used, or first mixing unit 12 may even be omitted.

Second mixing unit 14 comprises a second mixer 140 and a matrix material reservoir 142. Matrix reservoir 142 is coupled to second mixer 140 to supply matrix material to second mixer 140 and second mixer 140 is configured to mix the matrix material with the diluted sample material from first mixing unit 12.

In operation, liquid is moved from first mixing unit 12 to second mixing unit 14. Although a conduit 11 has been shown for this purpose, ti should be understood that a batch op liquid may be moved to second mixing unit 14 in any way. In another embodiment, second mixing unit 14 may be combined with first mixing unit 14. In second mixing unit 14 MALDI matrix material is added. MALDI matrix materials are known per se from the prior art. Matrix material may be used that is suitable to crystallize attached to micro-organisms and that has have an optical absorption band suitable for absorbing the laser pulses to ionize material from the micro-organisms. A wide range of suitable matrix materials is known. MALDI matrix materials that do not form crystals are also known. MALDI matrix material directed at specific types of organism or specific organic material may be used, but alternatively MALDI matrix material applicable to a wider range of organism and/or organic materials may be used. Second mixing unit 14 may be configured to add MALDI matrix material in an amount sufficient to provide a molar matrix to analyte ratio in the order of 100:1 to 10000:1.

The liquid obtained from second mixing unit 14 is pumped to an opening through piezo resonator 16 as a continuous stream of liquid via conduit 11. Although a conduit 11 directly connecting second mixing unit 14 to piezo resonator is shown, it should be understood that a batch of liquid may be transported from second mixing unit 14 to a position at an input of conduit 11 by any other means. An intermediate reservoir (not shown) may be used at the input of conduit 11. A liquid pump (not shown) may be used to pump a stream liquid through conduit 11 to piezo resonator 16, or a pump may be used to put pressure on the liquid in second mixing unit 14 or an intermediate reservoir to which the liquid has been moved in order to force the stream of liquid to piezo resonator 16 through conduit 11. Conduit 11 may be so short that effectively a direct connection from second mixing unit 14 or the intermediate reservoir to the opening through piezo resonator 16 is formed.

In an embodiment piezo resonator 16 comprises a frame, a membrane with an orifice with an opening of twenty micrometer at which the flow of liquid is directed and piezo-electric material coupled between the membrane and the frame. Preferably an opening of at least ten micrometer is used. The piezo-electric material is located to make the orifice move back and forth in the direction of the liquid flow. Electrodes are provided on the piezo-electric material to drive the motion.

In operation control circuit 17 applies a high frequency electric excitation to the electrodes. A frequency in a range of 1 kHz to 1 MHz may be used for example. The high frequency electric voltage causes periodic movement of the opening in the direction of the liquid flow, which cause the liquid stream to break up into parts, resulting in droplets. A series of droplets is launched along a flight path through chamber 15. Preferably, a constant setting of the excitation frequency of piezo resonator 16 is used, so that drops of the same size are produced. Techniques to control drop size are known per se from ink jet printing technology.

Although an exemplary embodiment has been described wherein a piezo resonator 16 is used to separate the stream of liquid into drops, it should be appreciated that other droplet forming techniques may be used.

In chamber 15 an atmosphere with a low pressure is maintained, for example in the range of a thousandth of a millibar to a few millibar. The atmosphere may consist of any gas. In an example normal air is used. The length of the flight path from piezo resonator 16 to the point of ionization is preferably at least so along that the time needed to traverse the flight path, given the speed of the drops, is sufficient to put the matrix in place, e.g. by crystallization. In an embodiment one or more intermediate nozzle skimmers may be used along the flight path to reduce the gas pressure until a level suitable for mass-spectroscopy is reached. In an embodiment mass spectroscopy is performed at pressures near $10^{-6}$ millibar, or more generally below $10^{-5}$ millibar. By using a low starting pressure at the stage where the drops are formed loss of drops before this pressure is reached can be kept low, which increases the efficiency of the apparatus. The fact that all drops are formed along the same flight path also increases efficiency. Preferably, drops are injected directly into the vacuum, but it may be desirable to add a stage at higher pressure to increase the stability of drop formation With drops of a size of a few micrometer (e.g. in the range between one and ten micrometer) the drops dry sufficiently to realize matrix formation (e.g. crystallization) within milliseconds or even within microseconds. With a speed of 20 m/sec this does not impose severe constraints on the length of the flight path. Even higher speeds in a range of 100-300 meters per second may be used.

A gas flow source (not shown) may be provided adjacent to piezo resonator 16 to create a gas jet along the flight path. Such a jet may help to reduce the chance that consecutive drops agglomerate.

Control circuit 17 controls pulse laser 18 to generate pulses in synchronism with oscillations of piezo resonator 16, with a relative phase so that pulses from pulse laser 18 will arrive in the flight path at the time points when droplets from piezo resonator 16 pass through the laser beam. This results in ionization of the particles from the droplets. Mass spectrometer 19 analyses the mass spectrum of the emerging particles.

The synchronization of laser pulses with oscillations of piezo resonator 16 may be realized by synchronizing the laser pulses to the excitation signal of piezo resonator 16. Alternatively, a droplet detector (not shown) may be used to detect droplets along the flight path in chamber 15 and pulsed laser 18 may be triggered by signals from such a detector. This detector may also be configured to measure droplet speed, to predict a time of arrival of each droplet. Alternatively, a predetermined speed may be assumed, which can be determined experimentally.

Mass spectra may be collected in control circuit 17, or in a measurement computer, and compared to reference spectra or parts of reference spectra or lists of biomarkers for known micro-organisms to identify the type of the micro-organisms in the respective drops. In a simple screening embodiment, a comparison with a small number of reference spectra may suffice. A count of identified micro-organisms may be computed, to determine a concentration of the identified micro-organisms by comparing the count with an overall count of drops, or with a count of drops that contain a micro-organism or cell of a reference type. In a more exploratory embodiment, a comparison with a larger number of reference spectrograms may be performed to identify a range of types of micro-organisms or cell types in the sample.

Figure 2:
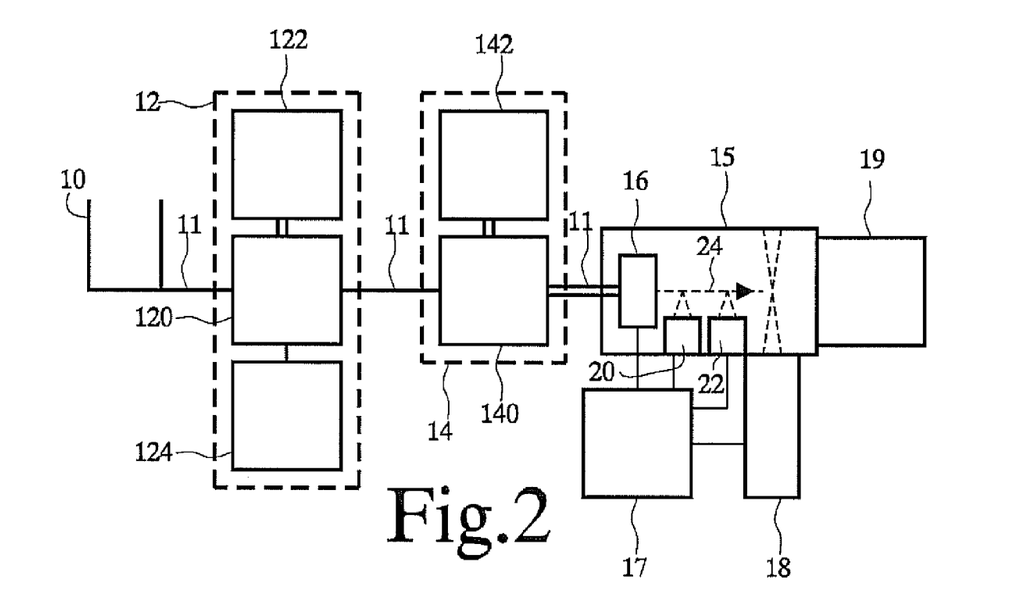
FIG. 2 shows an identification apparatus with fluorescent screening

FIG. 2 shows an embodiment that uses prescreening of droplets. A further laser 20 and a fluorescence detector 22 have been added. Further laser 20 has a wavelength selected to excite fluorescence of micro-organisms in the droplets. A wavelength of 266 nm may be used for example. Further laser 20 is directed at a part of the flight path 24 of droplets before they reach the point of ionization. A continuous wave laser may be used, or a pulsed laser synchronized to drop formation. Fluorescence detector 22 is similarly directed at the flight path 24, to capture fluorescence from a flying drop after irradiation by further laser 20. Fluorescence detector 22 is coupled to control circuit 17, which is configured to cause pulsed laser to fire conditionally, only at drops wherein fluorescence indicative of the presence of a micro-organism has been detected. Furthermore, further laser 20 may be used to trigger firing, that is, to select the time point of firing. In another embodiment one or more lasers may be used to trigger firing using time points and/or speeds of drops detected with the one or more lasers. This may be done independent of whether a further laser 20 is used.

In a further embodiment fluorescence may be detected in conduit 11, before separation of the liquid into drops at piezo resonator 16. In this case, further laser and fluorescence detector are directed at conduit 11 and control circuit 17 may determine the drop in which the micro-organism will be isolated from the time of detection, the flow speed to piezo resonator 16 and the excitation signal of piezo resonator 16. Detection of fluorescence in conduit 11 may help to prevent that matrix crystallization obstructs detection of fluorescence from the micro-organisms.

Figure 3:
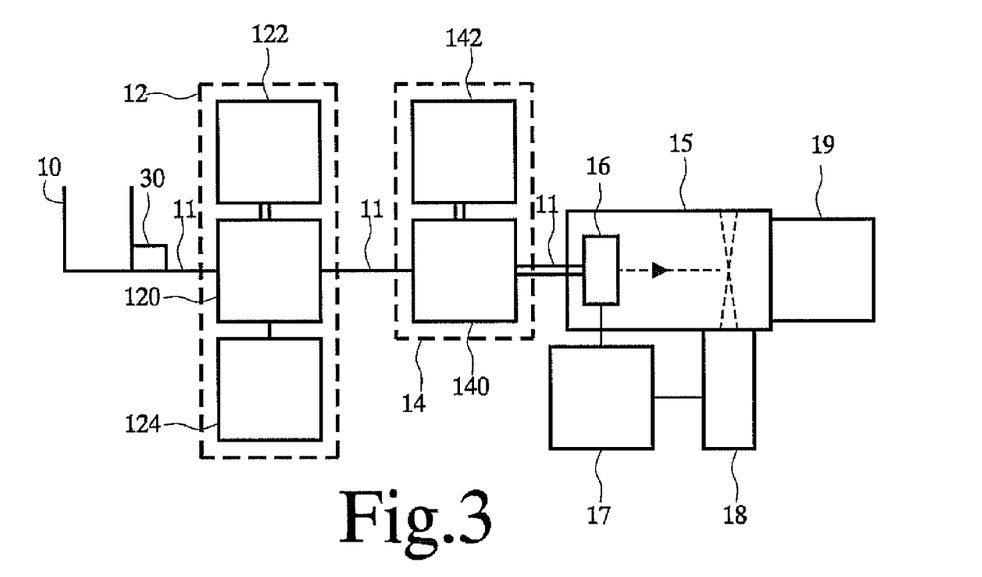
FIG. 3 shows an identification apparatus with an ultrasonic separator

FIG. 3 shows an embodiment wherein the apparatus comprises an ultrasound source 30 directed at sample receiver 10, or the conduit 11 between sample receiver 10 and first mixing unit 12 and configured to separate clusters of micro-organisms into individual micro-organisms. In addition ultrasound source 30 may be used to separate micro-organisms from a sample carrier on which the micro-organisms have been collected, such as a cotton swab or a piece of filtration paper.

Techniques for ultrasound separation of clusters of micro-organisms are known per se. Separation of clusters may be used to reduce the number of droplets in which more than one micro-organism is present at a time. Although an example is shown wherein ultrasound source 30 is directed at sample receiver 10, it should be appreciated that one or more ultrasound sources 30 may be directed at any position between sample receiver 10 and piezo resonator 16, for separating clusters. Separation of clusters before first mixing unit 12 has the advantage that a more reliable density determination and more homogeneous dilution may be obtained.

Instead of separating clusters by means of ultrasound, other separation techniques may be used, such as vortexing, which is known per se and which involve the creation of vortexes in the liquid, e.g. by shaking the liquid. Without separation of the clusters a risk exists that some drops may contain a cluster of micro-organisms. In some cases this may not be a problem, for example when the clusters are homogeneous, or when there is no need to distinguish between different types of organism in a cluster.

Figure 4:
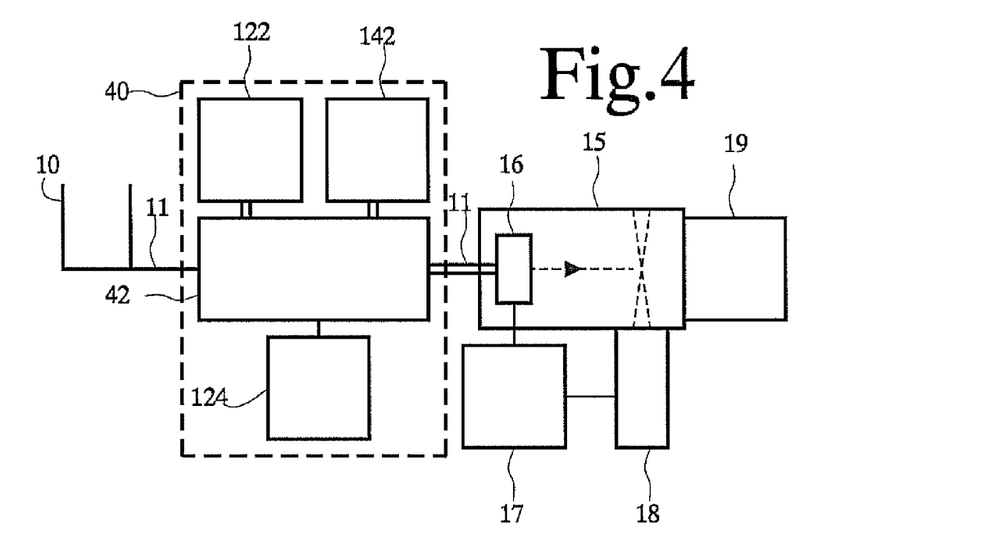
FIG. 4 shows an further identification apparatus
Figure 4A:
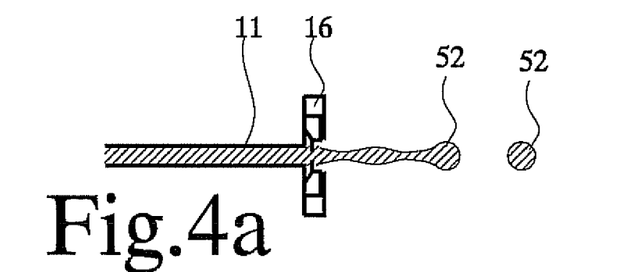
FIGS. 4a-c show examples of liquid stream separators
Figure 4B:
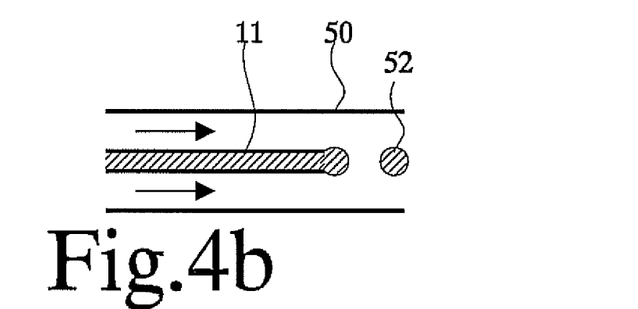

FIG. 4a schematically shows more detail of a separator with a piezo resonator 16. The conduit 11 ends at the opening through piezo resonator 16, which periodically constricts to launch drops. Although an embodiment has been described wherein a piezo resonator 16 is used to separate the stream of liquid into drops, it should be appreciated that other droplet forming techniques may be used. For example a gas dynamic nozzle may be used, which is known per se, wherein conduit 11 opens into a gas flow that acts to separate the stream of liquid into droplets when or after the stream is injected in the gas flow. FIG. 4b shows an example of a configuration may be used wherein the end of conduit 11 exhausts in a larger conduit 50 wherein the gas flow is supplied. Thus drops may be formed after injecting the stream of liquid into a gaseous environment. Preferably the gas and liquid flow rates and the opening size are set so a narrow range of droplet sizes is obtained, as this increases efficiency and simplifies control needed to ensure that pulsed laser 18 fires at the time needed to hit a droplet.

Figure 4C:
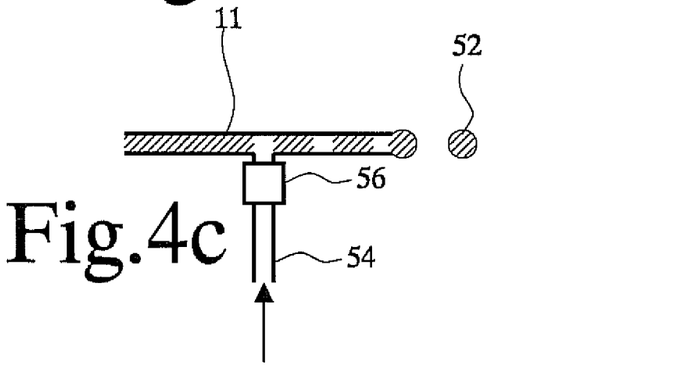

In another embodiment a drop separation mechanism, similar to dripping from a tap may be used, wherein a stream of liquid is forced through a conduit to an opening of the conduit and drops are torn off into flight from the opening. Gravity, or a gas flow past the opening may be used to tear of drops from the opening. In this embodiment drop size may be controlled by means of selection of flow rate of the stream of liquid, diameter and/or shape of the opening and gas flow speed. In another embodiment, a gas inlet 54 into conduit 11 as shown in FIG. 4c may be used to inject gas bubbles at regularly spaced distances into the stream of liquid through conduit 11. A valve 56 in gas inlet 54 may be used to form the bubbles. The bubbles separate the stream into sections before the stream reaches the opening of conduit 11, so that each section will result in a respective drop when the stream is forced out of the opening of conduit 11.

As described, the apparatus provides for a process of identifying micro-organisms wherein a stream of liquid containing micro-organisms and matrix material. The liquid stream is broken up into droplets, preferably into monodisperse droplets. The droplets are supplied in flight along a flight path. These droplets are dried in the vacuum while in flight. The resulting dried particles are ionized to obtain a mass spectrogram. The particles are analyzed in flight. In the illustrated embodiment the liquid is diluted to a dilution level at which a majority of the drops with microorganism contain only one micro-organism.

Although a specific embodiment of an apparatus has been shown, it should be appreciated that this process may be performed with modified embodiments of the apparatus. For example, instead of using conduits 11, a transportable sample holder may be used, which may be transported to a diluent mixing unit, a matrix material mixing unit and a droplet forming station. Diluent mixing and matrix material mixing may be performed in a single mixing unit 40, as shown in FIG. 4, with a mixing stage 42 for mixing the sample both with diluent and matrix material, simultaneously or in different time intervals. Part of the transport may be performed in conduits and another part may be performed with a transport units. The sequence of dilution and addition of matrix material may be changed, or any mixing step may be split in a plurality of mixing steps.

Although applications to micro-organisms have been described by way of example, it should be appreciated the technique can be use to identify other types of biological material, such as cells, for example blood cells or specific types of such cells. The sample may contain a mix of various materials and a plurality of types of material may be identified from the sample, by combining results obtained from mass-spectrograms of different drops.

In a hospital admission screening application, a sample of biological material may be taken from a patient, for example from saliva, or from any mucous membrane or a blood sample or a urine sample or combinations thereof, and the sample may be processed as described. The resulting identifications of micro-organisms in drops from their mass spectrograms, or a count of drops that contain a micro-organism with a mass spectrogram that matches the reference mass spectrogram of a harmful micro-organism such as a Staphylococcus Aureus with a specific antibiotic resistance may be used to decide whether or not to accept the patient for normal treatment. Patients with harmful micro-organisms may be redirected for special treatment.

Similarly, outbreaks of infections with harmful micro-organisms may be monitored by taking samples from a plurality of patients and processing the samples as described. In an embodiment samples from different patients may be mixed, for example if identification of harmful micro-organisms in a group of people is needed, e.g. in a hospital ward, without need to single out individual patients.

In a diagnostic application, a sample of biological material may be taken from a patient, and the sample may be processed as described to detect infection with specific micro-organisms.

Although an embodiment with a pulsed laser has been described, which avoids the need to supply sufficient power for ionization continuously, it should be appreciated that the separate nature of the drops may make it possible to use a continuous wave laser. Instead of a laser, other types of light source may be used to provide light for ionizing at least part of a drop. UV light or infrared light may be used for example. Instead of light, other means for ionizing may be considered such as ion bombardment or even ultrasound irradiation.

Figure 5:
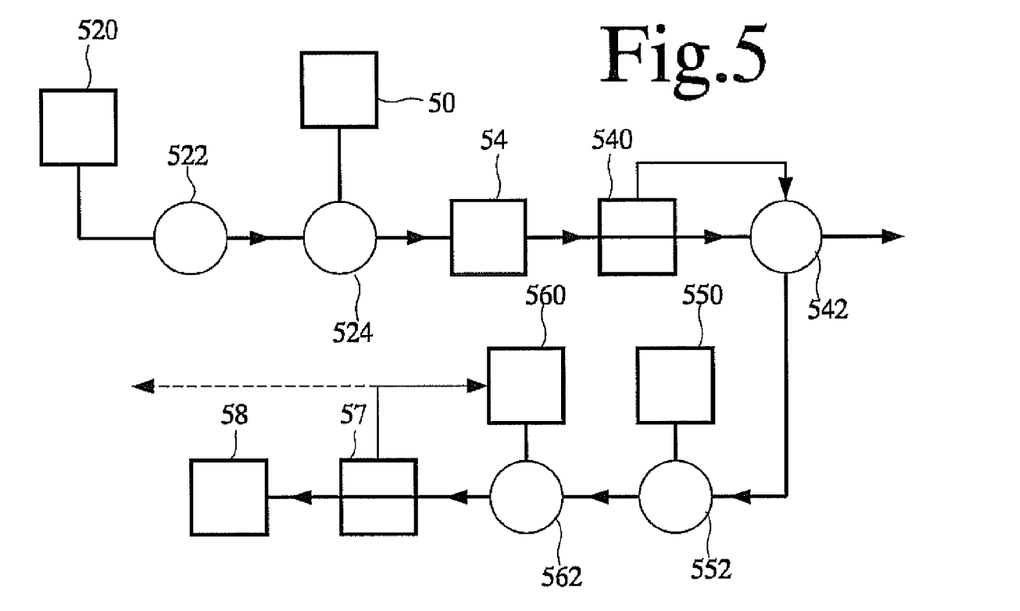
FIG. 5-7 show embodiments of an identification apparatus

FIG. 5 shows an identification apparatus comprising a sample reservoir 50, a first carrier liquid reservoir 520, a pump 522, a first mixing stage 524, a Flow Field-Flow fractionator 54, a size detector 540, a three way valve 542, a matrix reservoir 550, a second mixing stage 552, a second carrier liquid reservoir 560, a third mixing stage 562, a flow cytometer 57 and a drop former 58. Pump 522, first mixing stage 524, Flow Field-Flow fractionator 54, three way valve 542, second mixing stage 552, third mixing stage 562 and drop former 58 are coupled in series along a liquid flow channel. First carrier liquid reservoir 520 feeds into an input of pump 522. Sample reservoir 50 feeds into an input of first mixing stage 524. Size detector 540 is coupled to a part of the liquid flow channel downstream from Flow Field-Flow fractionator 54 and upstream of three way valve 542. Matrix reservoir 550 feeds into an input of second mixing stage 552. Second carrier liquid reservoir 560 feeds into an input of third mixing stage 562. Flow cytometer 57 is coupled to a part of the liquid flow channel downstream from third mixing stage 562 and upstream of drop former 58.

Although not shown, the apparatus may contain buffers for storing variable amounts of liquids at one or more positions along the liquid flow channel, between three way valve 542 and second mixing stage 552 for example. The buffers may be used to reduce variations in flow rate.

In operation, pump 522 pumps carrier liquid from first carrier liquid reservoir 520 through the flow channel. Water may be used as carrier liquid for example, with an addition of ammonium acetate. First mixing stage 524 mixes a pulsed quantity of sample liquid into the stream of carrier liquid, during a pulse time interval. Flow Field-Flow fractionator 54 fractionates the stream into temporally successive fractions according to particle size. Size detector 540 detector detects a size of the particles as a function of time and it controls three way valve 542 to pass the flow to second mixing stage 552 or a waste output, dependent on the detected size. Second mixing stage 552 mixes MALDI matrix material from matrix reservoir 560 into the stream. Continuous mixing may be used. Third mixing stage 562 mixes additional carrier liquid into the stream. Flow cytometer 57 measures the density of micro-organisms in the stream. The mixing rate of third mixing stage 562 is controlled dependent on the measured density. Drop former 58 separates the stream into successive parts of the stream and launches drops, each formed from a respective part.

Preferably the flow channel is designed so that the stream flows from second mixing stage 552 to drop former 58 without any substantial axial rearrangement. That is, large reservoirs where the liquid can accumulated and mix are avoided in the flow-channel. As a result, that parts into which drop former 58 separates the liquid correspond to successive sections of the stream already after second mixing stage 552, or at least after third mixing stage 562. The dilution at third mixing stage 562 is performed by mixing carrier liquid into the flowing stream.

A feedback loop may be used to control third mixing stage 562, the feedback loop being designed to change the mixing rate upward or downward according to whether the measured density "C" is above or below a preset target value. A preset target value C0 may be used that satisfies C0*V=A, where V is the volume of a part into which drop former 58 separates the stream and A is a number below two, and more preferably below one; a value A=0.2 may be used for example. When the density drops so low that it remains below the preset target value even if no carrier liquid, or a predetermined minimum of carrier liquid is added, control of third mixing stage 562 may cease to be dependent of the density.

Instead of Flow Field-Flow fractionator 54 any other fractionating device may be used that fractionates the stream with a pulse of sample liquid into a stream with gradually changing particle size. This has the advantage that it reduces the amount of relatively small sized material from the sample that could obstruct identification of micro-organisms when present in the drops. Furthermore, it has the advantage that the rate of mixing in third mixing stage 562 can be adapted in time to provide for micro-organism density differences between different fractions of micro-organisms. Thus drops with a single micro-organism can be more easily realized for each of the fractions. When fractions with widely different density are simultaneously present this may be difficult.

A conventional Flow Field-Flow fractionator 54 may be used. Such a column is described for example in the article by Hookeun Lee et al., cited in the preceding. Briefly, such an apparatus uses a thin ribbon like open channel through which a stream of carrier liquid with sample material flows. Different flow speeds arise as a function of position in the channel transverse to the flow direction. By means of an external field different transverse density distributions are realized for different fractions of particles. An external field such as an electric field, an imposed temperature gradient, gravity etc, may used. The density distribution arises from a balance between the effect of the field and diffusion that counteracts the density gradient. As a result different fractions will emerge at the output of the Flow Field-Flow fractionator 54 separated by time, leaving micro-organisms intact.

Size detector 540 serves to detect the size of the particles of the emerging fractions. Size detector 540 may be omitted when a tightly controlled Flow Field-Flow fractionation process is used. In this case three way valve 542 may be controlled by a timer for example, that defines time intervals for passing liquid towards second mixing stage 552 at predetermined delays after the pulses of sample material. Size detector 540 may be configured to measure light scattering as a measure of size, but other techniques such as conductivity measurements or detection of fluorescence may be used.

Flow cytometer 57 may comprise a fluorescence detector configured to detect temporal peaks in fluorescence in passing liquid that are due to micro-organisms. Fluorescence at a wavelength corresponding to NADH may be used for example. A count of such peaks per time unit may be used as a density signal to control third mixing stage 562. In an embodiment, detections of individual microorganisms from flow cytometer 57 may be used to enable laser firing of the pulse laser (not shown), firing at a drop being disabled when flow cytometer 57 does not detect a micro-organism in the part of the liquid stream from which the drop will be formed. When the density of micro-organisms drops below a level at which third mixing stage 562 mixes carrier liquid dependent on organism density, control of firing may be used to maintain efficient mass spectroscopy.

Figure 6:
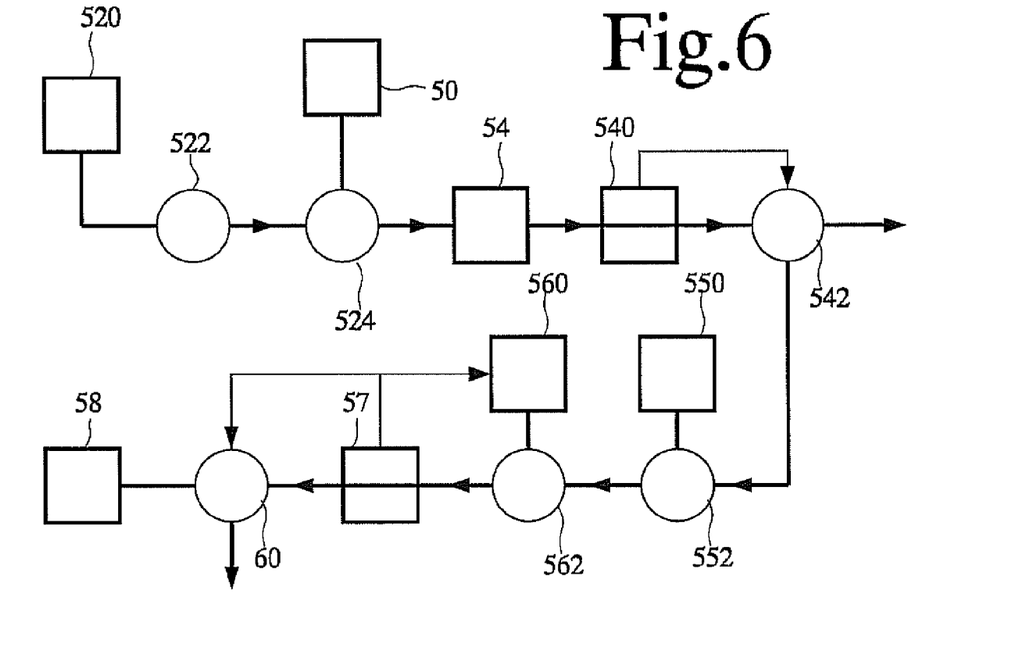
Figure 7:
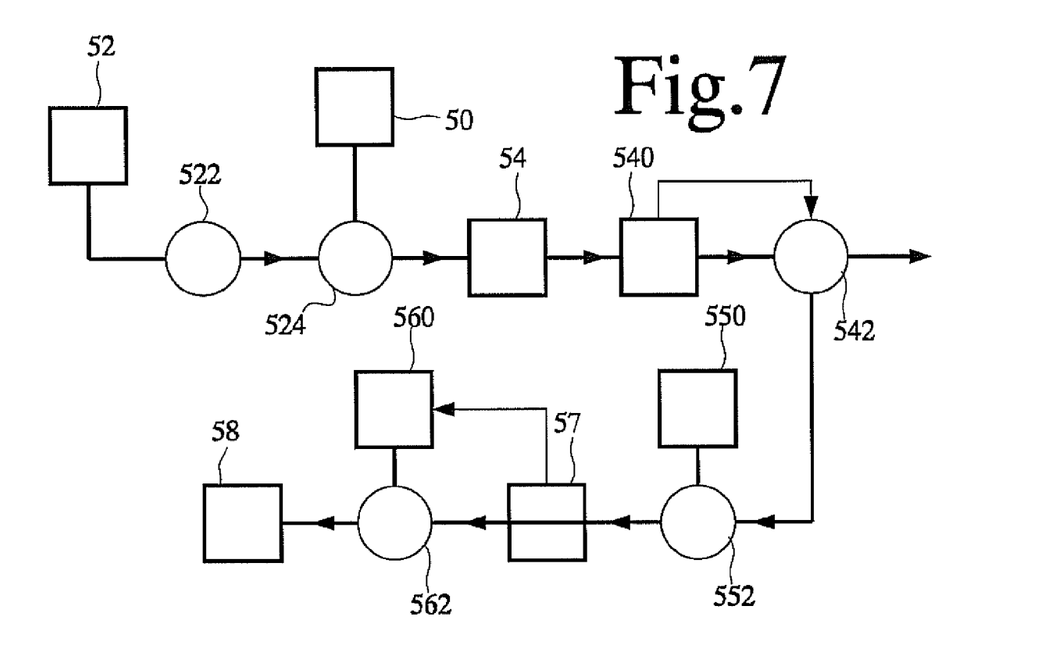

FIG. 6 shows an apparatus with an additional three way valve 60 between flow cytometer 57 and drop former 58, with a control input coupled to flow cytometer 57. In operation detections of individual microorganisms are used to control additional three way valve 60, making it pass liquid to drop former 58 when a microorganism is detected and to a waste output otherwise. In this way the number of useless drops is minimized. When the density of micro-organisms drops below a level at which third mixing stage 562 mixes carrier liquid dependent on organism density, control of waste output may be used to maintain efficient mass spectroscopy. In an embodiment, "on demand" control of drop former 58 is used, to trigger drop forming when the liquid is not fed to the waste output. FIG. 7 shows an apparatus wherein flow cytometer 57 is located upstream of third mixing stage 562. Thus a feed forward control is realized according to a predetermined relation between detected micro-organism density and mixing rate. The following relation may be used $$F_{add} = N_{org} * V_{drop}/A \cdot F_{in}$$

Herein $F_{add}$ is the mixed in flow rate from second carrier liquid reservoir 560, $N_{org}$ is the incoming density of detected microorganisms per unit time, $V_{drop}$ is the volume of the liquid part from which a drop is formed and A is a desired density, A preferably being less than one, for example A=0.2. In the feedback solutions of FIGS. 5 and 6 this relation is realized by feedback. Density may be determined by counting detected micro-organisms or from the time distance between successive detections. In an embodiment, third mixing stage 562 of the embodiment of FIG. 7 may be controlled dependent on detection of individual microorganisms, the mixing rate being controlled dependent on the time distance between successive detections of organisms, increasing the amount of added carrier liquid when the time distance decreases.

The feed forward solution of FIG. 7 has the advantage that it makes it possible to provide for detection from smaller samples. The feed forward solution may be combined with use of additional three way valve 60 (not shown) or enabling of firing. In this case, the control may be statistical, preventing firing when only a low percentage of drops contains micro-organisms. Although an embodiment has been shown wherein flow cytometer 57 is located between second and third mixing stage 552, 562. It should be appreciated that flow cytometer 57 may also be located upstream of second mixing stage 562. In this case the density is measured before the addition of MALDI matrix material. When second mixing stage 562 is designed to add MALDI matrix material at a known rate, the density of micro-organisms in the stream before second mixing stage 562 can be translated into a density after this stage. For better control a flow cytometer 57 after second mixing stage 562 is preferred.

The density measurement from cytomer 57 of FIG. 7 may be used to control laser firing and/or an additional three way valve (not shown). The additional three way valve may be located at a similar position as three way valve 60 in FIG. 6, or between flow cytomer 57 and third mixing stage 552. In an embodiment size detector 54 may be replaced by a cytometer, which controls three way valve 542 to pass liquid to second mixing stage 552 upon detection of at least a threshold density of microorganisms. In this case this cytometer may also be used to control dilution by third mixing stage 562. But, although a single cytometer has been shown both multiple purposes, it should be appreciated that instead a plurality of cytometers may be used, each for implementing a respective one or groups of these purposes.

In an embodiment a flow cytometer upstream of drop former 58 may be used to control firing of pulse laser 18 even without measures to control dilution. This may be used for example when it is known that the density of micro-organisms will never be too high. In another embodiment a flow cytometer upstream of drop former 58 may be used to control a three way valve to supply liquid to drop former 58 selectively upon the detection of microorganisms or detection that a density of micro-organisms execeeds a threshold value. This may be done even without measures to control dilution. A combination of control of laser firing and a three way valve may be used.

Thus, an apparatus for identifying biological material in a sample may be provided, the apparatus comprising

- a stream generator configured to supply a continuous stream of a liquid wherein the sample and a crystal forming matrix material have been mixed;
- a liquid portion separator configured to separate the stream into successive parts of the stream and to supply drops formed from said parts in flight along a flight path;
- a radiation source directed at the flight path and configured to supply radiation for ionizing material from the drops;
- a mass spectrometer configured to obtain mass spectrograms of the ionized material from individual ones of the drops; and
- a cytometer located between stream generator and the liquid portion separator and configured to detect microorganisms in the stream, the cytometer being coupled to the radiation source and/or to a flow path selector enabling the radiation source and/or controlling selection between directing the stream to the liquid portion separator or elsewhere dependent on detection of microorganisms. In this way the apparatus can be made to process small samples of microorganisms with higher efficiency.

Although use of three way valves has been described to realize a flow path selector, to switch between passing liquid for further processing and wasting the liquid, it should be appreciated that other types of valve may be used for this, such as manifolds.

A plurality of branches with Flow Field-Flow fractionators 54 may be used in parallel to handle different samples. Each branch may contain the components corresponding to those up to and including three way value 542 for example. A liquid manifold may be used to connect these branches to the input of second mixing stage 552 successively. Thus efficient use can be made of the apparatus, even if Flow Field-Flow fractionation takes a lot of time.

A method of identifying biological material in a sample is provided, the method comprising preparing a liquid comprising the sample and a MALDI matrix material; generating a continuous stream of the liquid; separating the stream into successive parts to form flying drops; ionizing material from the drops while in flight; and measuring mass spectra from the ionized material.

The biological material comprises micro-organisms. The method may comprise diluting the sample or the liquid to a dilution level corresponding to a concentration of less than one micro-organism on average in a volume of individual ones of the parts. The dilution level may be measured and the dilution may be controlled to proceed until the liquid has been diluted to said concentration. A cluster separation step may be applied to the sample or the liquid to separate clusters of micro-organisms into individual micro-organisms before the separating step.

The liquid may be separated into parts of substantially equal volume, for example by separating the successive parts at regular intervals in said stream. The successive parts of liquid may be launched into flight during or after separating them from the stream. Alternatively, the stream may be launched into flight and the stream may be separated into the successive parts while in the stream is in flight. The drops may be dried in flight, at least to a drying level where crystals of the matrix material are formed in flight, prior to the ionizing step. A gas jet may be applied along at least part of a trajectory of the drops in flight. The drops may be screened based on fluorescence before said ionizing, and ionizing only drops with parts of the liquid that has been detected to produce at least a predetermined fluorescence intensity.

An apparatus is provided for identifying biological material in a sample, the apparatus comprising a mixer configured to prepare a liquid wherein the sample and a crystal forming matrix material are mixed; a stream generator configured to supply a continuous stream of the liquid; a liquid portion separator configured to separate the stream into parts and to supply drops formed from said parts in flight along a flight path; a radiation source directed at the flight path and configured to supply radiation for ionizing material from the drops; and a mass spectrometer configured to obtain mass spectrograms of the ionized material from individual ones of the drops.

The invention claimed is:

1. A method of identifying biological material that comprises micro-organisms in a sample, the method comprising:
   preparing a liquid comprising the sample;
   generating a continuous stream of the liquid;
   diluting the liquid to a dilution level dependent on a measured density of the micro-organisms, to a dilution level corresponding to a density C of microorganisms that satisfies C*V<1, wherein V is a volume per separated part, said diluting being performed by mixing carrier liquid into the stream downstream from the generation of the stream;
   adding a MALDI matrix material to the liquid;
   separating the stream into successive parts of the stream, to form flying drops;
   ionizing material from the drops while in flight;
- measuring mass spectra from the ionized material.

2. A method according to claim 1, comprising measuring the density of the micro-organisms in the stream with a cytometer and controlling said diluting dependent on a cytometer output result.

3. A method according to claim 2, wherein said measuring with the cytometer in the stream is performed upstream of said diluting on said stream or a precursor stream that flows into the stream when the MALDI matrix is added to the precursor stream.

4. A method according to claim 1, comprising comparing said measured density with a threshold value and disabling said ionizing when the density is below the threshold value.

5. A method according to claim 1, wherein the density is measured with a cytometer downstream from said diluting and upstream of separation of the stream into parts, the method comprising selecting individual ones of the parts for said ionizing dependent on detection of micro-organisms by the cytometer.

6. A method according to claim 1, comprising fractionating the liquid into a flow that successively comprises particles of different size, diluting the flow, measuring the density of the micro-organisms after said fractionating and controlling said diluting dependent on the measured density of the micro-organisms.

7. A method according to claim 6, wherein said fractionating comprises applying flow field-flow fractionation.

8. A method according to claim 1, comprising separating the liquid into parts of substantially equal volume.

9. A method according to claim 1, comprising applying a cluster separation step to the sample or the liquid to separate clusters of micro-organisms into individual micro-organisms before the separating step.

10. A method according to claim 1, comprising controlling a flow rate F of carrier liquid that dilutes the liquid according to $$F=N_{org}*V_{drop}/A-F_{in}$$

wherein $N_{org}$ is the incoming density of detected microorganisms per unit time, $V_{drop}$ is the volume of the liquid part from which a drop is formed, $F_{in}$ is an incoming flow rate of the stream and A is a target density less than one.

11. An apparatus for identifying biological material in a sample, the apparatus comprising:
- a stream generator configured to supply a continuous stream of a liquid comprising the sample;
- a mixing unit downstream form the stream generator, comprising a mixer and a detector for measuring a density of micro-organisms, a dilution level of the mixer being controlled dependent on a measured density of the micro-organisms, to a dilution level corresponding to a concentration C of microorganisms that satisfies C*V<1, wherein V is a volume per separated part;
- means for adding a MALDI matrix material to the liquid;
- a liquid portion separator configured to separate the stream into successive parts of the stream and to supply drops formed from said parts in flight along a flight path;
- a radiation source directed at the flight path and configured to supply radiation for ionizing material from the drops;
- a mass spectrometer configured to obtain mass spectrograms of the ionized material from individual ones of the drops.

12. An apparatus according to claim 11, wherein the detector comprises a cytometer configured to measure the density in the stream or in a precursor stream that flows into the stream when the MALDI matrix is added to the precursor stream.

13. A method of detecting bacteria with resistance against an antibiotic the method comprising identifying the bacteria from a mass spectrum obtained by the method of claim 1.

14. A method of determining whether to give special treatment to a patient in a hospital, the method comprising:
- taking a sample of biological material from the patient;
- preparing a liquid comprising the sample;
- generating a continuous stream of the liquid;
- diluting the sample or the liquid to a dilution level dependent on a measured density of the micro-organisms, to a dilution level corresponding to a concentration C of microorganisms that satisfies C*V<1, wherein V is a volume per separated part, said diluting being performed by mixing carrier liquid into the stream downstream from the generation of the stream;

adding a MALDI matrix material to the liquid;

separating the stream into successive parts of the stream, to form flying drops;

ionizing material from the drops while the drops are in flight;

measuring mass spectrograms for individual ones of the drops;

isolating the patient when the mass spectrogram for at least part of the drops matches the mass spectrum of a predetermined micro-organism.

15. A method of monitoring for outbreaks of an infection with a predetermined micro-organism in a hospital, the method comprising:

taking samples of biological material from at least two patients;

preparing a liquid or liquids comprising the sample and/or samples from respective patients;

generating a continuous stream or continuous streams of the liquid or liquids;

diluting the sample or the liquid to a dilution level dependent on a measured density of the micro-organisms, to a dilution level corresponding to a concentration C of microorganisms that satisfies C*V<1, wherein V is a volume per separated part, said diluting being performed by mixing carrier liquid into the stream downstream from the generation of the stream;

separating the stream or streams into successive parts to form flying drops;

ionizing material from the drops while the drops are in flight;

measuring mass spectra for individual ones of the drops;

generating an infection alert when the mass spectra for at least part of the drops matches the mass spectrum of a predetermined micro-organism.

* * * * *